United States Patent
Pasquali et al.

(10) Patent No.: US 9,402,825 B2
(45) Date of Patent: *Aug. 2, 2016

(54) DRY POWDER FORMULATION COMPRISING AN ANTICHOLINERGIC, A CORTICOSTEROID AND A BETA-ADRENERGIC FOR ADMINISTRATION BY INHALATION

(71) Applicant: CHIESI FARMACEUTICI S.p.A., Parma (IT)

(72) Inventors: Irene Pasquali, Parma (IT); Rossella Musa, Parma (IT); Francesca Schiaretti, Parma (IT); Azita Askey-Sarvar, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/327,920

(22) Filed: Jul. 10, 2014

(65) Prior Publication Data

US 2015/0017248 A1    Jan. 15, 2015

(30) Foreign Application Priority Data

Jul. 11, 2013  (EP) ..................... 13176114
Nov. 28, 2013  (EP) ..................... 13194763

(51) Int. Cl.
*A61K 9/14*   (2006.01)
*A61K 9/72*   (2006.01)
*A61K 31/40*  (2006.01)
*A61K 9/00*   (2006.01)
*A61K 31/167* (2006.01)
*A61K 31/573* (2006.01)
*A61K 45/06*  (2006.01)

(52) U.S. Cl.
CPC ............... *A61K 31/40* (2013.01); *A61K 9/0075* (2013.01); *A61K 31/167* (2013.01); *A61K 31/573* (2013.01); *A61K 45/06* (2013.01); *Y10S 514/958* (2013.01)

(58) Field of Classification Search
None
See application file for complete search history.

(56) References Cited

U.S. PATENT DOCUMENTS

| | | | |
|---|---|---|---|
| 8,778,402 B2 * | 7/2014 | Monari | A61K 9/14 424/489 |
| 2004/0202616 A1 | 10/2004 | Keller et al. | |
| 2007/0202053 A1 * | 8/2007 | Bilzi et al. | 424/46 |
| 2007/0212422 A1 | 9/2007 | Keller et al. | |
| 2008/0127972 A1 * | 6/2008 | Morton | 128/203.15 |
| 2010/0055192 A1 * | 3/2010 | Musa et al. | 424/489 |
| 2011/0262543 A1 | 10/2011 | Cocconi et al. | |
| 2011/0308519 A1 * | 12/2011 | Schiaretti | 128/203.15 |
| 2014/0322142 A1 | 10/2014 | Pasquali et al. | |

FOREIGN PATENT DOCUMENTS

| | | |
|---|---|---|
| WO | WO 0178693 A2 * | 10/2001 |
| WO | 2008/000482 | 1/2008 |
| WO | 2011/076841 | 6/2011 |
| WO | 2011/105975 | 9/2011 |
| WO | 2011/120779 | 10/2011 |
| WO | 2013/110632 | 8/2013 |

OTHER PUBLICATIONS

European Search Report in Application No. 131761140.0 issued on Jan. 3, 2014.
European Search Report in Application No. 13194763.2 issued on Feb. 10, 2014.
Chew N Y K et al., "Journal of Pharmacy and Pharmaceutical Sciences, Canadian Society for Pharmaceutical Sciences", vol. 5, No. 2, (2002) pp. 162-168.
Y.Rahimpour et al., Advanced Pharmaceutical Bulletin, vol. 2, pp. 183-187 (2012).
U.S. Appl. No. 14/724,056, filed May 28, 2015, Brambilla et al.

* cited by examiner

*Primary Examiner* — Isaac Shomer
(74) *Attorney, Agent, or Firm* — Oblon, McClelland, Maier & Neustadt, L.L.P.

(57) ABSTRACT

Dry powder formulations for inhalation comprising a combination of an anticholinergic, a long-acting beta$_2$-adrenoceptor agonist, and a corticosteroid are useful for the prevention and/or treatment of inflammatory and/or obstructive airways diseases.

16 Claims, No Drawings

DRY POWDER FORMULATION COMPRISING AN ANTICHOLINERGIC, A CORTICOSTEROID AND A BETA-ADRENERGIC FOR ADMINISTRATION BY INHALATION

CROSS REFERENCES TO RELATED APPLICATIONS

This application claims priority to European Patent Application No. 13176114.0, filed on Jul. 11, 2013 and European Patent Application No. 13194763.2, filed on Nov. 28, 2013, both of which are incorporated herein by reference in their entireties.

BACKGROUND OF THE INVENTION

1. Field of the Invention

The present invention relates to formulations for administration by inhalation by means of dry powder inhalers. In particular, the present invention relates to dry powder formulations comprising a combination of an anticholinergic, a beta$_2$-adrenoceptor agonist, and an inhaled corticosteroid, process for their preparation and use thereof for the prevention and/or treatment of respiratory diseases.

2. Discussion of the Background

Respiratory diseases are a common and important cause of illness and death around the world. In fact, many people are affected by inflammatory and/or obstructive lung diseases, a category characterized by inflamed and easily collapsible airways, obstruction to airflow, problems exhaling and frequent medical clinic visits and hospitalizations. Types of inflammatory and/or obstructive lung disease include asthma, bronchiectasis, bronchitis and chronic obstructive pulmonary disease (COPD).

In particular, chronic obstructive pulmonary disease (COPD) is a multi-component disease characterized by airflow limitation and airway inflammation. Exacerbations of COPD have a considerable impact on the quality of life, daily activities and general well-being of patients and are a great burden on the health system. Thus, the aims of COPD management include not only relieving symptoms and preventing disease progression but also preventing and treating exacerbations.

While available therapies improve clinical symptoms and decrease airway inflammation, they do not unequivocally slow long-term progression or address all disease components. With the burden of COPD continuing to increase, research into new and improved treatment strategies to optimize pharmacotherapy is ongoing, and in particular, combination therapies, with a view to their complementary modes of action enabling multiple components of the disease to be addressed. Evidence from recent clinical trials indicates that triple therapy, combining an anticholinergic with an inhaled corticosteroid, and a long-acting $\beta_2$-adrenoceptor agonist, may provide clinical benefits additional to those associated with each treatment alone in patients with more severe COPD.

Currently, there are several recommended classes of therapy for COPD, of which bronchodilators such as $\beta_2$-agonists and anticholinergics are the mainstay of symptom management in mild and moderate disease, prescribed on an as-needed basis for mild COPD and as a maintenance therapy for moderate COPD.

Said bronchodilators are efficiently administered by inhalation, thus increasing the therapeutic index and reducing side effects of the active material.

For the treatment of more severe COPD, guidelines recommend the addition of inhaled corticosteroids (ICSs) to long-acting bronchodilator therapy. Combinations of therapies have been investigated with a view to their complementary modes of action enabling multiple components of the disease to be addressed. Data from recent clinical trials indicate that triple therapy, combining an anticholinergic with an ICS and a long-acting $\beta_2$-agonist (LABA), may provide clinical benefits additional to those associated with each treatment alone in patients with moderate to severe COPD.

An interesting triple combination, presently under investigation, includes:
  i) formoterol, particularly its fumarate salt (hereinafter indicated as FF), a long acting beta-2 adrenergic receptor agonist, currently used clinically in the treatment of bronchial asthma, COPD and related disorders;
  ii) glycopyrronium bromide, an anticholinergic recently approved for the maintenance treatment of COPD;
  iii) beclometasone dipropionate (BDP) a potent anti-inflammatory corticosteroid steroid, available under a wide number of brands for the prophylaxis and/or treatment of asthma and other respiratory disorders.

Formulations for pressurized metered dose inhalers (pMDIs) containing all said three active ingredients in combination are disclosed in WO 2011/076841 and WO 2011/076843, which are incorporated herein by reference in their entireties.

However, despite their popularity, pMDI formulations may have some disadvantages in particular in elderly patients, mostly due to their difficulty to synchronize actuation from the device with inspiration.

Dry powder inhalers (DPIs) are a valid alternative to MDIs for the administration of drugs to airways and lung. Active ingredients intended for inhalation as dry powders should be used in the form of micronized particles.

In order to manufacture a single suitable DPI product containing said kinds of active ingredients, the dry powder formulation should have acceptable flowability to facilitate both handling and the aerosol performance of all three actives from the device.

This is challenging task, as it is well known that by increasing the numbers and the concentration of the active ingredients, the higher is the risk of forming uneven agglomerates which are detrimental to the possibility of achieving a good uniformity of distribution of the active ingredient in the powder mixture and hence a good accuracy of the dose. Said phenomenon has also a detrimental effect on the flowability of the relevant formulation, which in turn would impact on the capability of the device of delivering the correct dose due to the active particles being unable to leave the inhaler and remaining adhered to its interior.

Therefore, the presence of three active ingredients with different physical and chemical properties to be delivered at three different dosage strengths within the same device creates serious problems in the preparation of homogenous blends as well as in the delivery of them with suitable respirable fractions.

WO 01/78693, which is incorporated herein by reference in its entirety, discloses a technology platform for preparing a dry powder formulation comprising as a carrier, a combination of a fraction of coarse excipient particles and a fine fraction made of fine excipient particles and magnesium stearate.

The formulation therein disclosed is described as freely flowable, physically and chemically stable and capable of delivering both accurate doses and a high fraction of fine active particles (respirable fraction).

However, there are no examples reported demonstrating that said platform would be suitable for a combination of three different active ingredients.

Furthermore, good results in terms of respirable fraction are only obtained if the fine fraction of the carrier is prepared starting from coarse excipient particles and the additive, and subjecting them to co-milling for long times, at least two hours, or to jet-milling.

Therefore it would be highly advantageous to provide a powder formulation for administration with DPIs comprising a combination of an anticholinergic, an inhaled corticosteroid, and a long-acting $\beta_2$-agonist as active ingredients, overcoming all the aforementioned disadvantages.

SUMMARY OF THE INVENTION

Accordingly, it is one object of the present invention to provide novel powder formulations for administration with a DPI comprising a combination of an anticholinergic, an inhaled corticosteroid, and a long-acting $\beta_2$-agonist as active ingredients.

It is another object of the present invention to provide novel DPIs which contain such a formulation.

It is another object of the present invention to provide novel methods of preparing such a formulation.

It is another object of the present invention to provide novel methods of preventing/treating certain diseases and/or conditions by administering an effective amount of such a composition.

These and other objects, which will become apparent during the following detailed description, have been achieved by the inventors' discovery of dry powder formulations for use in a dry powder inhaler (DPI) comprising:

a) a fraction of fine particles, prepared by co-mixing in a high-energy apparatus for a period of less than 20 minutes, consisting of a mixture of 90 to 99.5 percent by weight of micronized particles of a physiologically acceptable excipient and 0.5 to 10 percent by weight of magnesium stearate, wherein at least 90% of all said particles have a volume diameter lower than 15 micron, preferably lower than 12 micron, and the volume median diameter of said particles is comprised between 3 and 7 micron, preferably between 4 and 6 micron;

b) a fraction of coarse particles consisting of a physiologically acceptable excipient having a mass median diameter equal to or higher than 100 micron, wherein the ratio between the fine particles and the coarse particles being between 1:99 and 30:70 percent by weight; and c) micronized particles of an anticholinergic, an inhaled corticosteroid (ICS), and a long-acting $\beta_2$-agonist (LABA) as active ingredients.

Preferably, the LABA is formoterol fumarate dihydrate, the ICS is beclometasone dipropionate and the anticholinergic is glycopyrronium bromide.

In a second aspect, the present invention provides dry powder formulations for use in a dry powder inhaler (DPI) comprising:

a) a fraction of fine particles consisting of a mixture of 90 to 99.5 percent by weight of particles of a physiologically acceptable excipient and 0.5 to 10 percent by weight of magnesium stearate, wherein at least 90% of all said particles have a volume diameter lower than 15 micron, preferably lower than 12 micron, and the volume median diameter of said particles is comprised between 3 and 7 micron, preferably between 4 and 6 micron;

b) a fraction of coarse particles consisting of a physiologically acceptable excipient having a mass median diameter equal to or higher than 100 micron, wherein the ratio between the fine particles and the coarse particles being between 1:99 and 30:70 percent by weight; and c) micronized particles of an anticholinergic, an inhaled corticosteroid (ICS), and a long-acting $\beta_2$-agonist (LABA) as active ingredients, wherein the at least 90% of all said micronized particles of the active ingredients have a volume diameter equal to or lower than 6.0 micron, preferably equal to or lower than 5.0 micron, and the volume median diameter of said particles is comprised between 1.2 and 2.5 micron, preferably between 1.3 and 2.2 micron.

Preferably, the LABA is formoterol fumarate dihydrate, the ICS is beclometasone dipropionate and the anticholinergic is glycopyrronium bromide.

In a third aspect, the present invention provides dry powder formulations for use in a dry powder inhaler (DPI) comprising:

a) a fraction of fine particles consisting of a mixture of 90 to 99.5 percent by weight of particles of alpha-lactose monohydrate and 0.5 to 10 percent by weight of magnesium stearate, wherein at least 90% of said particles have a volume diameter lower than 12 micron, and the volume median diameter of said particles is comprised between 4 and 6 micron;

b) a fraction of coarse particles consisting of alpha-lactose monohydrate having a mass median diameter equal to or higher than 175 micron, wherein the ratio between the fine particles and the coarse particles being between 5:95 and 15:85 percent by weight; and c) micronized particles of formoterol fumarate dihydrate, glycopyrronium bromide, and optionally beclometasone dipropionate as active ingredients, wherein the at least 90% of all said micronized particles of the active ingredients have a volume diameter lower than 6.0 micron, preferably equal to or lower than 5.0 micron, and the volume median diameter of said particles is comprised between 1.2 and 2.5 micron, preferably between 1.3 and 2.2 micron.

In a fourth aspect, the present invention provides processes for preparing the aforementioned dry powder formulations.

In a fifth aspect, the present invention provides dry powder inhaler devices filled with the above dry powder formulations.

In a sixth aspect, the present invention provides such formulations for use in the prevention and/or treatment of an inflammatory and/or obstructive airways disease, in particular chronic obstructive pulmonary disease (COPD).

In a seventh aspect, the present invention provides methods of preventing and/or treating an inflammatory and/or obstructive airways disease, in particular chronic obstructive pulmonary disease (COPD), which comprises administering by inhalation of an effective amount of such a formulation.

In an eighth aspect, the present invention provides the use of such formulations in the manufacture of a medicament for the prevention and/or treatment of an inflammatory and/or obstructive airways disease in particular chronic obstructive pulmonary disease (COPD).

DETAILED DESCRIPTION OF THE PREFERRED EMBODIMENTS

The terms "muscarinic receptor antagonists," "antimuscarinic drugs," and "anticholinergic drugs" can be used synonymously.

The term "pharmaceutically acceptable salt of glycopyrrolate" refers to a salt of the compound (3S,2'R), (3R,2'S)-3-

[(cyclopentylhydroxyphenylacetyl)oxy]-1,1-dimethylpyrrolidinium in approximately 1:1 racemic mixture, also known as glycopyrronium salt.

The term "pharmaceutically acceptable salt of formoterol" refers to a salt of the compound 2'-hydroxy-5'-[(RS)-1-hydroxy-2 {[(RS)-p-methoxy-α-methylphenethyl]amino}ethyl]formanilide.

The term "beclometasone dipropionate" refers to the compound (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[α]phenanthren-17-yl propionate.

The term "pharmaceutically acceptable salt" comprises inorganic and organic salts. Examples of organic salts may include formate, acetate, trifluoroacetate, propionate, butyrate, lactate, citrate, tartrate, malate, maleate, succinate, methanesulfonate, benzenesulfonate, xinafoate, pamoate, and benzoate. Examples of inorganic salts may include fluoride chloride, bromide, iodide, phosphate, nitrate and sulphate.

The expression "high energy apparatus" refers to an apparatus that generates high compression and shear forces (mechanical energy) achieved by repeated compression of the powder bed in the centrifugal field.

The term "micronized" refers to a substance having a size of few microns.

The term "coarse" refers to a substance having a size of one or few hundred microns.

In general terms, the particle size of particles is quantified by measuring a characteristic equivalent sphere diameter, known as volume diameter, by laser diffraction.

The particle size can also be quantified by measuring the mass diameter by means of suitable known instrument such as, for instance, the sieve analyzer.

The volume diameter (VD) is related to the mass diameter (MD) by the density of the particles (assuming a size independent density for the particles).

In the present application, the particle size of the active ingredients and of fraction of fine particles is expressed in terms of volume diameter, while that of the coarse particles is expressed in terms of mass diameter.

The particles have a normal (Gaussian) distribution which is defined in terms of the volume or mass median diameter (VMD or MMD) which corresponds to the volume or mass diameter of 50 percent by weight of the particles, and, optionally, in terms of volume or mass diameter of 10% and 90% of the particles, respectively.

Another common approach to define the particle size distribution is to cite three values: i) the median diameter d(0.5) which is the diameter where 50% of the distribution is above and 50% is below; ii) d(0.9), where 90% of the distribution is below this value; iii) d(0.1), where 10% of the distribution is below this value.

The span is the width of the distribution based on the 10%, 50% and 90% quantile and is calculated according to the formula.

$$\text{Span} = \frac{D[v, 0.9] - D[v, 0.1]}{D[v, 0.5]}$$

In general terms, particles having the same or a similar VMD or MMD can have a different particle size distribution, and in particular a different width of the Gaussian distribution as represented by the d(0.1) and d(0.9) values.

Upon aerosolization, the particle size is expressed as mass aerodynamic diameter (MAD), while the particle size distribution is expressed in terms of mass median aerodynamic diameter (MMAD) and Geometric Standard Deviation (GSD). The MAD indicates the capability of the particles of being transported suspended in an air stream. The MMAD corresponds to the mass aerodynamic diameter of 50 percent by weight of the particles.

In the final formulation, the particle size of the active ingredients can be determined by scanning electron microscopy according to methods known to the skilled person in the art.

The term "hard pellets" refers to spherical or semispherical units whose core is made of coarse excipient particles.

The term "spheronization" refers to the process of rounding off of the particles which occurs during the treatment.

The term "good flowability" refers to a formulation that is easy handled during the manufacturing process and is able to ensure an accurate and reproducible delivery of the therapeutically effective dose.

Flow characteristics can be evaluated by different tests such as angle of repose, Carr's index, Hausner ratio or flow rate through an orifice.

In the context of the present invention, the flow properties were tested by measuring the flow rate through an orifice according to the method described in the European Pharmacopeia (Eur. Ph.) 7.3, $7^{th}$ Edition, which is incorporated herein by reference in its entirety.

The expression "good homogeneity" refers to a powder wherein, upon mixing, the uniformity of distribution of a component, expressed as coefficient of variation (CV) also known as relative standard deviation (RSD), is less than 5.0%. It is usually determined according to known methods, for instance by taking samples from different parts of the powder and testing the component by HPLC or other equivalent analytical methods.

The expression "respirable fraction" refers to an index of the percentage of active particles which would reach the lungs in a patient.

The respirable fraction is evaluated using a suitable in vitro apparatus such as Andersen Cascade Impactor (ACI), Multi Stage Liquid Impinger (MLSI) or Next Generation Impactor (NGI), according to procedures reported in common Pharmacopoeias, in particular in the European Pharmacopeia (Eur. Ph.) 7.3, $7^{th}$ Edition, which is incorporated herein by reference in its entirety.

It is calculated by the percentage ratio of the fine particle mass (formerly fine particle dose) to the delivered dose.

The delivered dose is calculated from the cumulative deposition in the apparatus, while the fine particle mass is calculated from the deposition of particles having a diameter <5.0 microns.

In the context of the present invention, the formulation is defined as an extrafine formulation when it is capable of delivering a fraction of particles having a particle size equal or less than 2.0 microns equal to or higher than 20%, preferably equal to or higher than 25%, more preferably equal to or higher than 30% and/or it is capable of delivering a fraction of particles having a particle size equal or less than 1.0 micron equal to or higher than 10%.

The expression "physically stable in the device before use" refers to a formulation wherein the active particles do not substantially segregate and/or detach from the surface of the carrier particles both during manufacturing of the dry powder and in the delivery device before use. The tendency to segregate can be evaluated according to Staniforth et al. J. Pharm. Pharmacol. 34, 700-706, 1982, which is incorporated herein by reference in its entirety, and it is considered acceptable if the distribution of the active ingredient in the powder formulation after the test, expressed as relative standard deviation (RSD), does not change significantly with respect to that of the formulation before the test.

The expression "chemically stable" refers to a formulation that, upon storage, meets the requirements of the EMEA Guideline CPMP/QWP/122/02 referring to 'Stability Testing of Existing Active Substances and Related Finished Products,' which is incorporated herein by reference in its entirety.

The term "surface coating" refers to the covering of the surface of the carrier particles by forming a film of magnesium stearate around said particles. The thickness of the film has been estimated by X-ray photoelectron spectroscopy (XPS) to be approximately of less than 10 nm. The percentage of surface coating indicates the extent by which magnesium stearate coats the surface of all the carrier particles.

The term "prevention" means an approach for reducing the risk of onset of a disease.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. The term can also mean prolonging survival as compared to expected survival if not receiving treatment.

According to the Global Initiative for Asthma (GINA), which is incorporated herein by reference in its entirety, "severe persistent asthma" is defined as a form characterized by daily symptoms, frequent exacerbations, frequent nocturnal asthma symptoms, limitation of physical activities, forced expiratory volume in one second ($FEV_1$) equal to or less than 60% predicted and with a variability higher than 30%.

According to the Global initiative for chronic Obstructive Pulmonary Disease (GOLD) guidelines, which is incorporated herein by reference in its entirety, "severe COPD" is a form characterized by a ratio between $FEV_1$ and the Forced Vital Capacity (FVC) lower than 0.7 and $FEV_1$ between 30% and 50% predicted. The very severe form is further characterized by chronic respiratory failure.

"Therapeutically effective dose" means the quantity of active ingredients administered at one time by inhalation upon actuation of the inhaler. Said dose may be delivered in one or more actuations, preferably one actuation (shot) of the inhaler. "Actuation" refers to the release of active ingredients from the device by a single activation (e.g. mechanical or breath).

The present invention is directed to dry powder formulations for use in a dry powder inhaler (DPI) comprising a fraction of fine excipients particles a), a fraction of coarse excipient particles b), and micronized particles of an anticholinergic, an inhaled corticosteroid (ICS), and a long-acting $\beta_2$-agonist (LABA) as active ingredients.

The LABA active ingredients, that may be present in form of pharmaceutically acceptable salts and/or solvate form thereof, can be selected from the group, which includes, but it is not limited to, formoterol, salmeterol, indacaterol, and vilanterol.

The anticholinergics, that are usually present in form of pharmaceutically acceptable inorganic salts, can be selected from the group which includes, but it is not limited to, glycopyrronium bromide or chloride, tiotropium bromide, and aclidinium bromide.

The ICS, that may be anhydrous or present in form of hydrates, can be selected from the group which includes, but it is not limited to, beclomethasone dipropionate and its monohydrate form, budesonide, fluticasone propionate, fluticasone furoate, and mometasone furoate.

Preferably, the LABA is formoterol fumarate dihydrate, the ICS is beclometasone dipropionate, and the anticholinergic is glycopyrronium bromide.

The fractions a) and b) are the "carrier" particles.

The fraction of fine particles a) is prepared by co-mixing in a high-energy apparatus for a period of less than 30 minutes.

Said fraction consists of 90 to 99.5 percent by weight of micronized particles of a physiologically acceptable excipient and 0.5 to 10 percent by weight of magnesium stearate (optionally micronized), wherein at least 90% of said particles have a volume diameter lower than 15 micron, preferably lower than 12 micron, and the volume median diameter of said particles is comprised between 3 and 7 micron, preferably between 4 and 6 micron.

Since the co-mixing step does not alter the particle size of the fraction of said particles, the person skilled in the art shall select the suitable size of the fine particles of the physiologically acceptable excipient as well as of magnesium stearate to achieve the desired particle size distribution in terms of both volume diameter of 90% of the particles and volume median diameter (50%).

Materials of the desired particle size distribution are commercially available.

In a preferred embodiment of the present invention, no more than 10% of said particles have a diameter lower than 1.8 micron, preferably lower than 1.5 micron.

The last feature is considered particular advantageous as a fraction of fine particles a) containing a higher amount of finer particles might create problems of flowability of the whole powder formulation.

It has been found that the technology platform disclosed in WO 01/78693, which is incorporated herein by reference in its entirety, might be suitable for preparing a dry powder formulation comprising three different active ingredients at different therapeutically effective dosages.

However, the inventors found that the fraction of fine particles constituting part of the carrier can be obtained in a much shorter time by subjecting the micronized excipient of the desired particle size and magnesium stearate (optionally micronized) to co-mixing in particular apparatus rather than co-milling coarse particles of the excipient with magnesium stearate.

Besides reducing the time of processing, this also improves the versatility of the formulation, as in this way it would be possible to target the final particle size of the fine fraction a) by pre-selecting it, as the co-mixing step does not affect the size of the particles, while by co-milling it isn't so easy to control the particle size of the final fine blend.

In comparison to what reported in WO 01/78693, which is incorporated herein by reference in its entirety, it has also surprisingly been found that, by carrying out the co-mixing step in particular apparatus, it is possible to provide formulations capable of delivering respirable fractions for each active ingredient higher than 50%.

The formulation according to the present invention also shows a good homogeneity of the active ingredients, a good flowability and adequate physical and chemical stability in the inhaler before use for pharmaceutical purposes.

In an embodiment of the invention, the fraction of fine particles a) may be prepared by co-mixing in a mechano-fusion apparatus.

Mechano-fusion is a simple, dry mechanical process that is designed to apply thin layers of lubricants to the particle surfaces without impacting on the original size of the particles.

The fine excipient particles and the magnesium stearate particles are fed into the mechano-Fusion driven vessel, where they are subject to a centrifugal force and are pressed against the vessel inner wall. The powder is compressed between the fixed clearance of the drum wall and a curved inner element with high relative speed between drum and element. The inner wall and the curved element together form a gap or nip in which the particles are pressed together. As a result the particles experience very high shear forces and very strong compressive stresses as they are trapped between the inner drum wall and the inner element (which has a greater curvature than the inner drum wall).

The particles violently collide against each other with enough energy to locally heat and soften, break, distort, flatten and wrap the particles of hydrophobic material around the core particle to form a coating. The energy is generally sufficient to break up agglomerates, while the particle size of the excipient particles remains substantially the same and a high extent of coating with magnesium stearate is achieved.

Either the outer vessel or the inner element may rotate to provide the relative movement. The gap between these surfaces is relatively small, and is typically less than 10 mm and is preferably less than 5 mm, more preferably less than 3 mm. This gap is fixed, and consequently leads to a better control of the compressive energy than is provided in some other forms of mill such as ball mills. Also, preferably, no impaction of milling media surfaces is present so that wear and consequently contamination are minimized.

A scraper may also be present to break up any caked material building up on the vessel surface. The local temperature may be controlled by use of a heating/cooling jacked built into the drum vessel walls. The powder may be re-circulated through the vessel.

Apparatus such as Nobilta™ and Nanocular™ mechano-fusion processors from Hosokawa Micron Corporation, Japan, are preferably utilized. Both systems comprise a cylindrical vessel with a rotating axial shaft (rotor). In the Nobilta™ processor, the paddles extend along the length of the axial shaft, and extend out to within approximately 1 mm of the vessel wall. Consequently, as the shaft rotates, the blades continuously sweep close to the vessel wall, ensuring all the powder is in constant and violent motion. Due to the high rotational speed of the paddles, the powder is propelled towards the wall, and as a result the mixture experiences very high shear forces at the paddle face, and compressive stresses between wall and paddle.

In the Nanocular™ processor, the motion is similar, but with less impact due to absence of the paddle faces, and a higher degree of compressive stresses between wall and press head.

The time of the process will depend on the specific processor, and it shall be suitably adjusted by the skilled person depending on the size of the batch. However, the process shall be carried out for a time no longer than 20 minutes, advantageously for a time comprised between 2 and 15 minutes, more advantageously for 10 minutes.

The product temperature remained constant during all the experiments. However, the temperature may be controlled in an accurate and reliable way by means of a cooling jacket system typically set a 15-25° C.

The speed of rotation shall depend on the specific mechano-fusion processor, type of rotor and related number of paddles, as well as on the size of the processed batch, and shall be suitably adjusted by the skilled person in the art.

Typically, a speed of rotation not higher than 5000 rpm may be utilized, advantageously comprised between 500 and 4000 rpm.

In an embodiment of the present invention, the particles are processed at 500 rpm for ten minutes.

In an alternative embodiment of the present invention, the fraction of fine particles a) may be prepared by co-mixing in a high energy mixer based on friction, operating at a rotation speed comprised between 100 rpm and 2500 rpm, preferably between 500 and 2000 rpm, more preferably between 1000 and 1500 rpm.

A typical high energy mixer which could be employed for carrying out the process of the invention is the CYCLO-MIX™ apparatus (Hosokawa Micron Group Ltd). Said apparatus comprises a stationary conical vessel fitted with paddle-shaped mixing elements, which rotate close to the inner vessel wall.

The powder loaded into the conical mixing vessel from the top; the degree of filling can range between 30 and 100%. Together, the rotation of the paddles and the conical shape of the vessel force the powder from the bottom to the upper zone of the vessel. Upon reaching the top, the powder flows downwards into the center of the vessel. This flow pattern results in fast mixing. During the upward motion, the particles of the powder are accelerated by the paddles and intensively mixed by friction with vessel. Such effects are sufficient to soften, break, distort, flatten and wrap the particles of magnesium stearate around the carrier particles to form a coating.

The product temperature remained constant during all the experiments. However, the temperature may be controlled in an accurate and reliable way by means of a cooling jacket system typically set a 15-25° C.

When the process is carried within the claimed limits in terms of rotating speed, the particle size of the excipient particles remain substantially the same and a high extent of coating with magnesium stearate is achieved.

The time of the process may be suitably adjusted by the skilled person in the art depending on the size of the batch.

However, the process shall be carried out for a time no longer than 20 minutes, advantageously for a time comprised between 2 and 15 minutes, preferably for a time equal to or lesser than 10 minutes.

Advantageously, the fine and coarse excipient particles may consist of any pharmacologically inert, physiologically acceptable material or combination thereof; preferred excipients are those made of crystalline sugars, in particular lactose; the most preferred are those made of $\alpha$-lactose monohydrate.

Preferably, the coarse excipient particles and the fine excipient particles both consist of $\alpha$-lactose monohydrate.

Advantageously, magnesium stearate coats the surface of the excipient particles of fine fraction a) in such a way that the extent of the surface coating is at least of 10%, more advantageously, higher than 20%.

In some embodiments, depending on the amount of magnesium stearate used as well as on the processing conditions, an extent of the surface coating higher than 50%, preferably higher than 60% could be achieved.

The extent to which the magnesium stearate coats the surface of the excipient particles may be determined by X-ray photoelectron spectroscopy (XPS), a well-known tool for determining the extent as well as the uniformity of distribution of certain elements on the surface of other substances. In the XPS instrument, photons of a specific energy are used to excite the electronic states of atoms below the surface of the sample. Electrons ejected from the surface are energy filtered via a hemispherical analyser (HSA) before the intensity for a defined energy is recorded by a detector. Since core level electrons in solid-state atoms are quantized, the resulting energy spectra exhibit resonance peaks characteristic of the electronic structure for atoms at the sample surface.

Typically XPS measurements are taken on an Axis-Ultra instrument available from Kratos Analytical (Manchester, UK) using monochromated Al Kα radiation (1486.6 eV) operated at 15 mA emission current and 10 kV anode potential (150 W). A low energy electron flood gun is used to compensate for insulator charging. Survey scans, from which quantification of the detected elements are obtained, are acquired with analyser pass energy of 160 eV and a 1 eV step size. High-resolution scans of the C 1s, O 1s, Mg 2s, N 1s and Cl 2p regions are acquired with pass energy of 40 eV and a 0.1 eV step size. The area examined is approximately 700 μm×300 μm for the survey scans and a 110 μm diameter spot for the high-resolution scans.

In the context of the present invention, by XPS, it is possible to calculate both the extent of coating and the depth of the magnesium sterate film around the lactose particles. The extent of magnesium stearate (MgSt) coating is estimated using the following equation:

$$\% \text{ MgSt coating} = Mg_{sample}/\% \ Mg_{ref}) \times 100$$

where:

$Mg_{sample}$ is the amount of Mg in the analyzed mixture;
$Mg_{ref}$ is the amount of Mg in the reference sample of commercially available MgSt.

Usually the values are calculated as a mean of two different measurements. Typically, an accuracy of 10% is quoted for routinely performed XPS experiments.

Alternatively, when the excipient particles are made of lactose, preferably of alpha-lactose monohydrate, the extent of surface coating may be determined by water contact angle measurement, and then by applying the equation known in the literature as Cassie and Baxter, for example cited at page 338 of Colombo I et al *Il Farmaco* 1984, 39(10), 328-341, which is incorporated herein by reference in its entirey, and reported below.

$$\cos \theta_{mixture} = f_{MgSt} * \cos \theta_{MgSt} + f_{lactose} \cos \theta_{lactose}$$

where:

$f_{MgSt}$ and $f_{lactose}$ are the surface area fractions of magnesium stearate and of lactose;
$\theta_{MgSt}$ is the water contact angle of magnesium stearate;
$\theta_{lactose}$ is the water contact angle of lactose
$\theta_{mixture}$ are the experimental contact angle values.

For the purpose of the present invention, the contact angle may be determined with methods that are essentially based on a goniometric measurement. These imply the direct observation of the angle formed between the solid substrate and the liquid under testing. It is therefore quite simple to carry out, being the only limitation related to possible bias stemming from intra-operator variability. It should be, however, underlined that this drawback can be overcome by adoption of a fully automated procedure, such as a computer assisted image analysis. A particularly useful approach is the sessile or static drop method which is typically carried out by depositing a liquid drop onto the surface of the powder in form of disc obtained by compaction (compressed powder disc method).

Within the limits of the experimental error, a good consistency has been found between the values of extent of coating as determined by XPS measurements, and those as estimated by the theoretical calculations based on the Cassie and Baxter equation.

The extent to which the magnesium stearate coats the surface of the excipient particles may also be determined by scanning electron microscopy (SEM), a well-known versatile analytical technique.

Such microscopy may be equipped with an EDX analyzer (an Electron Dispersive X-ray analyzer), that can produce an image selective to certain types of atoms, for example magnesium atoms. In this manner it is possible to obtain a clear data set on the distribution of magnesium stearate on the surface of the excipient particles.

SEM may alternatively be combined with IR or Raman spectroscopy for determining the extent of coating, according to known procedures.

Optionally, the fraction of fine particles a) may be subjected to a conditioning step according to the conditions disclosed in WO 2011/131663, which is incorporated herein by reference in its entirety.

The coarse excipient particles of the fraction b) must have mass median diameter equal to or higher than 100 micron preferably equal to or greater than 125 micron, more preferably equal to or greater than 150 micron, even more preferably equal to or greater than 175 micron.

Advantageously, all the coarse particles have a mass diameter in the range 50-1000 micron, preferably comprised between 60 and 500 micron.

In certain embodiments of the present invention, the mass diameter of said coarse particles might be comprised between 80 and 200 micron, preferably between 90 and 150 micron, while in another embodiment, the mass diameter might be comprised between 200 and 400 micron, preferably between 210 and 355 micron.

In a preferred embodiment of the present invention, the mass diameter of the coarse particles is comprised between 210 and 355 micron.

In general, the person skilled in the art shall select the most appropriate size of the coarse excipient particles by sieving, using a proper classifier.

When the mass diameter of the coarse particles is comprised between 200 and 400 micron, the coarse excipient particles preferably have a relatively highly fissured surface, that is, on which there are clefts and valleys and other recessed regions, referred to herein collectively as fissures. The "relatively highly fissured" coarse particles can be defined in terms of fissure index or rugosity coefficient as described in WO 01/78695 and WO 01/78693, both of which are incorporated herein by reference in their entireties, and they could be characterized according to the description therein reported. Advantageously, the fissure index of said coarse particles is of at least 1.25, preferably of at least 1.5, more preferably of at least 2.0, while the rugosity coefficient is of at least 1.25.

Said coarse particles may also be characterized in terms of tapped density or total intrusion volume measured as reported in WO 01/78695, which is incorporated herein by reference in its entirety.

The tapped density of said coarse particles could advantageously be less than 0.8 g/cm$^3$, preferably between 0.8 and 0.5 g/cm$^3$. The total intrusion volume could be of at least 0.8 cm$^3$, preferably at least 0.9 cm$^3$.

The ratio between the fraction of fine particles a) and the fraction of coarse particles b) shall be comprised between 1:99 and 30:70% by weight, preferably between 2:98 and 20:80% by weight.

In a preferred embodiment, the ratio is comprised between 5:95 and 15:85% by weight.

In certain embodiments, the ratio is of 10:90 by weight, while in other embodiments, the ratio might be 5:95 by weight.

The step of mixing the coarse excipient particles b) with the fraction of fine particles a) is typically carried out in suitable mixers, e.g. tumbler mixers such as Turbula™ or Dynamix™, rotary mixers, or instant mixer such as Diosna™, for at least 5 minutes, preferably for at least 30 minutes, more preferably for at least two hours.

In a general way, the person skilled in the art shall adjust the time of mixing and the speed of rotation of the mixer to obtain a homogenous mixture.

When spheronized coarse excipient particles are desired to obtain hard-pellets according to the definition reported above, the step of mixing shall be typically carried out for at least four hours.

Advantageously, each active ingredient is present in the formulation of the invention in a crystalline form, more preferably with a crystallinity degree higher than 95%, even more preferably higher than 98%, as determined according to known methods.

Since the formulation of the present invention should be administered to the lungs by inhalation, at least 90% of the micronized particles of each active ingredient should have a volume diameter equal to or lower than 6 micron.

On the other hand, it is well known that most of the available formulations tend to be associated with a poor therapeutic control of individuals exhibiting respiratory diseases affecting the small airways such as the small airways asthma phenotype.

Therefore there is need of "extrafine" formulations of inhaled corticosteroids in combination with long-acting β-agonists and anticholinergics which could reach the distal tract of the respiratory tree and hence improving small airways outcomes and associated control.

Accordingly, in a particular embodiment of the present invention, the micronized particles of each active ingredient are characterized by a selected, narrow, and well defined particle size distribution capable of reaching said distal tract of the respiratory tree.

Therefore, the invention is also directed to a dry powder formulation for use in a dry powder inhaler (DPI) comprising:

a) a fraction of fine particles consisting of a mixture of 90 to 99.5 percent by weight of particles of a physiologically acceptable excipient and 0.5 to 10 percent by weight of magnesium stearate, wherein at least 90% of all said particles have a volume diameter lower than 15 micron, preferably lower than 12 micron, and the volume median diameter of said particles is comprised between 3 and 7 micron, preferably between 4 and 6 micron;

b) a fraction of coarse particles consisting of a physiologically acceptable excipient having a mass median diameter equal to or higher than 100 micron, wherein the ratio between the fine particles and the coarse particles being between 1:99 and 30:70 percent by weight; and c) micronized particles of an anticholinergic, an inhaled corticosteroid (ICS), and a long-acting $\beta_2$-agonist (LABA) as active ingredients, wherein the at least 90% of all said micronized particles of the active ingredients have a volume diameter lower than 6.0 micron, preferably equal to or lower than 5.0 micron, and the volume median diameter of said particles is comprised between 1.2 and 2.5 micron, preferably between 1.3 and 2.2 micron.

In this case, the fraction of fine particles a) could be obtained according to any of the methods disclosed in WO 01/78693, which is incorporated herein by reference in its entirety, for example by co-milling or by co-mixing as reported on page 15, lines 5-15. In an alternative embodiment, it might be obtained by co-mixing in a high-energy apparatus according to the conditions disclosed in the present application.

Preferably, the LABA is formoterol fumarate dihydrate, the ICS is beclometasone dipropionate and the anticholinergic is glycopyrronium bromide.

Advantageously, no more than 10% of all said micronized particles of the active ingredients have a diameter lower than 0.6 micron, preferably equal to or lower than 0.7 micron, more preferably equal to or lower than 0.8 micron.

It follows that the width of the particle size distribution of the particles of each active ingredient, expressed as a span, should be advantageously comprised between 1.0 and 4.5, more advantageously between 1.2 and 3.0, preferably between 1.3 and 2.1, more preferably between 1.6 and 2.0. According the Chew et al J Pharm Pharmaceut Sci 2002, 5, 162-168, which is incorporated herein by reference in its entirety, the span corresponds to [d (v, 0.9)–d(v, 0.1)]/d(v, 0.5).

Even more advantageously, at least 99% of said particles [d(v, 0.99)] shall have a volume diameter equal to or lower than 7.0 micron, and substantially all the particles have a volume diameter comprised between 6.8 and 0.4 micron, preferably between 6.5 and 0.45 micron.

The size of the particles active is determined by measuring the characteristic equivalent sphere diameter, known as volume diameter, by laser diffraction. In the reported examples, the volume diameter has been determined using a Malvern apparatus. However, other equivalent apparatus may be used by the skilled person in the art.

In order to provide an extrafine formulation comprising formoterol fumarate dihydrate, BDP, and glycopyrronium bromide as active ingredients, it would also be preferable that the micronized particles of BDP have a Specific Surface Area comprised between 5.5 and 7.0 m$^2$/g, preferably between 5.9 and 6.8 m$^2$/g, the micronized particles of formoterol fumarate dihydrate have a Specific Surface Area comprised between 5 and 7.5 m$^2$/g, preferably between 5.2. and 6.5 m$^2$/g, more preferably between 5.5 and 5.8 m$^2$/g, and the micronized particles of glycopyrronium bromide have a Specific Surface Area comprised between 3.0 and 6.0 m$^2$/g, preferably between 3.5 and 4.5 m$^2$/g.

The Specific Surface Area is determined by Brunauer-Emmett-Teller (BET) nitrogen adsorption method according to a known procedure known.

All the micronized active ingredients utilized in the formulation of the invention may be prepared by processing in a suitable mill according to known methods.

In one embodiment of the invention, they could be prepared by grinding using a conventional fluid energy mill such as commercially available jet mill micronizers having grinding chambers of different diameters.

Depending on the type of the apparatus and size of the batch, the person skilled in the art shall suitably adjust the milling parameters such as the operating pressure, the feeding rate and other operating conditions to achieve the desired particle size.

In a particular embodiment, the micronized particles of glycopyrronium bromide may be prepared according to the process disclosed in EP 13165483.2, which is incorporated herein by reference in its entirety.

In a particularly preferred embodiment, the present invention is directed dry powder formulation for use in a dry powder inhaler (DPI) comprising:

a) a fraction of fine particles consisting of a mixture of 90 to 99.5 percent by weight of particles of alpha-lactose monohydrate and 0.5 to 10 percent by weight of magnesium stearate, wherein at least 90% of said particles have a volume diameter lower than 12 micron, and the volume median diameter of said particles is comprised between 4 and 6 micron;

b) a fraction of coarse particles consisting of alpha-lactose monohydrate having a mass median diameter equal to or higher than 175 micron, wherein the ratio between the fine particles and the coarse particles being between 5:95 and 15:85 percent by weight; and c) micronized particles of formoterol fumarate dihydrate, glycopyrronium bromide, and optionally beclometasone dipropionate as active ingredients, wherein the at least 90% of all said micronized particles of the active ingredients have a volume diameter lower than 6.0 micron, preferably equal to or lower than 5.0 micron, and the volume median diameter of said particles is comprised between 1.2 and 2.5 micron, preferably between 1.3 and 2.2 micron.

Advantageously, beclometasone dipropionate is present as third active ingredient.

The present invention is also related to processes for preparing the dry powder formulations disclosed herein comprising the step of mixing the fraction of fine particles a), the fraction of coarse lactose particles b) and all the micronized active ingredients.

In one embodiment, the carrier particles comprising the fraction of fine particles a) and the fraction of coarse particles b) may be prepared by mixing in suitable apparatus known to the skilled person in the art, for example a Turbula™ mixer. The two fractions are preferably mixed in a Turbula™ mixer operating at a rotation speed of 11 to 45 rpm, preferably 16 to 32 rpm for a period comprised between 30 and 300 minutes, preferably between 150 and 240 minutes.

Also the mixing of the carrier particles with the active ingredient particles may be carried out by mixing the components in suitable known apparatus, such as a Turbula™ or Dynamix™ mixer for a sufficient period to achieve the homogeneity of the active ingredient in the final mixture. Advantageously, the mixing is carried out for a time comprised between 30 and 120 minutes, preferably between 45 and 100 minutes.

Optionally, in an alternative embodiment, one active ingredient is first mixed with a portion of the carrier particles and the resulting blend is forced through a sieve, then, the two further active ingredients and the remaining part of the carrier particles are blended with the sieved mixture; finally, the resulting mixture is sieved through a sieve, and mixed again.

The skilled person in the art shall select the mesh size of the sieve depending on the particle size of the coarse particles.

In a particular embodiment, when the fraction of fine particles a) can be prepared according to any of the methods disclosed in WO 01/78693, which is incorporated herein by reference in its entirety, the powder formulation of the present invention might be prepared by co-mixing the micronized particles of the excipients, the particles of magnesium and the coarse excipients particles all together in a proper apparatus, followed by the addition of the micronized active ingredients to the resulting mixture, and mixing again.

The ratio between the carrier particles and the active ingredients will depend on the type of inhaler used and the required dose.

The powder formulations of the present invention may be suitable for delivering a therapeutic amount of all active ingredients in one or more actuations (shots or puffs) of the inhaler.

Advantageously, the formulations of the invention shall be suitable for delivering a therapeutically effective dose of all three active ingredients comprised between 50 and 600 μg, preferably between 100 and 500 μg.

For example, the formulations will be suitable for delivering 3-12 μg formoterol (as fumarate dihydrate) per actuation, especially 6 μg or 12 μg per actuation, 25-200 μg beclometasone dipropionate (BDP) per actuation, especially 50, 100 or 200 μg per actuation, and 10-65 μg glycopyrronium (as bromide), especially 12.5 μg or 25 μg.

The dry powder formulation of the invention may be utilized with any dry powder inhaler.

Dry powder inhaler (DPIs) can be divided into two basic types: i) single dose inhalers, for the administration of single subdivided doses of the active compound; each single dose is usually filled in a capsule; and ii) multidose inhalers preloaded with quantities of active principles sufficient for longer treatment cycles.

The dry powder formulations of the invention are particularly suitable for multidose DPIs comprising a reservoir from which individual therapeutic dosages can be withdrawn on demand through actuation of the device, for example that described in WO 2004/012801, which is incorporated herein by reference in its entirety.

Other multidose devices that may be used are, for instance, the DISKUS™ of GlaxoSmithKline, the TURBOHALER™ of AstraZeneca, the TWISTHALER™ of Schering and the CLICKHALER™ of Innovata.

As marketed examples of single dose devices, there may be mentioned ROTOHALER™ of GlaxoSmithKline, HANDIHALER™ of Boehringer Ingelheim, Breezehaler™ of Novartis, and Monodose RS01 of Plastiape.

In a preferred embodiment, when an extrafine formulation according to the invention is utilized, the dry powder formulation is filled in the DPI device disclosed in WO 2004/012801, which is incorporated herein by reference in its entirety, being particularly suitable for the delivery of extrafine formulation.

To protect the DPIs from ingress of moisture into the formulation, it may be desirable to overwrap the device in a flexible package capable of resisting moisture ingress such as that disclosed in EP 1760008, which is incorporated herein by reference in its entirety.

Administration of the formulations of the present invention is preferably indicated for the prevention and/or treatment of chronic obstructive pulmonary disease (COPD). However, said formulation might also be indicated for the prevention and/or treatment of asthma of all types and severity, including severe persistent asthma, as well as further respiratory disorders characterized by obstruction of the peripheral airways as a result of inflammation and presence of mucus such as chronic obstructive bronchiolitis.

In certain embodiments, the formulations of the present invention are suitable for the prevention and/or treatment of severe and/or very severe forms of respiratory disorders, in particular severe and/or very severe forms of COPD.

Other features of the invention will become apparent in the course of the following descriptions of exemplary embodiments which are given for illustration of the invention and are not intended to be limiting thereof.

EXAMPLES

Example 1

Preparation of the Fraction of Fine Particles a) by Mechano-Fusion

Several batches made of about 25 g micronized alpha-lactose monohydrate (Meggle, Germany) mixed with different amounts of magnesium stearate from Peter Greven, Germany (MgSt) were fed into the 100 ml driven vessel of the mechano-fusion apparatus AMS-MINI (Hosokawa Micron Corporation) equipped with two different rotors. The driven vessel was also equipped with a cooling jacket system set up at 15° C. The process was conducted according to the conditions reported in Table 1.

TABLE 1

| Batch | Rotation speed (rpm) | Processing time (min) | MgSt (%) |
|---|---|---|---|
| 1C | 3000 | 10 | 2 |
| 1D | 4000 | 10 | 2 |
| 2C | 3000 | 10 | 2 |
| 2D | 4000 | 10 | 2 |
| GK/A | 500 | 10 | 0.5 |
| GK/B | 500 | 10 | 1 |
| GK/C | 500 | 10 | 2 |
| GK/D | 500 | 10 | 3 |

The obtained mechano-fused microparticles were collected and subjected to technological characterization.

Example 2

Technological Characterization of the Fine Particles of Example 1

The fine particles as obtained in Example 1 were subjected to the following analyses.
Scanning Electron Microscopy (SEM).
Morphological properties were investigated using a scanning electron microscope (Phenom™, FEI Company, Hillsboro, Oreg.). Each sample was carefully mounted on a sample holder, so as to ensure representative images, and sputter coated with gold. SEM micrographs were taken using in-built image capture software.
Particle Size Distribution.
Particle size distributions were measured by laser diffraction (Mastersizer® S, Malvern Instruments, Worcestershire, UK). The parameter taken into consideration was the VD in micron of 10%, 50% and 90% of the particles expressed as d(v, 0.1), d(v, 0.5) and d(v, 0.9), respectively, which correspond to the mass diameter assuming a size independent density for the particles. The results are reported in Table 2.
Uniformity of Distribution.
The uniformity of distribution of MgSt was evaluated by withdrawing 12 samples from different parts of the powder, then its content determined by HPLC analysis. The results in terms of Relative Standard Deviation (RSD) are reported in Table 2 for batches GK/A, GK/B, GK/C, and GK/D.
MgSt Coating.
The extent to which the magnesium stearate coats the surface of the lactose particles was determined by X-ray photoelectron spectroscopy (XPS) using an Axis-Ultra instrument available from Kratos Analytical (Manchester, UK) and according to the conditions reported in the specification.

TABLE 2

| Batch | MgSt uniformity RSD | Particle size (μm) d(v0.1) | d(v0.5) | d(v0.9) | MgSt coating (%) |
|---|---|---|---|---|---|
| GK/A | 2.97 | 1.17 | 4.58 | 10.62 | 10.6 |
| GK/B | 2.26 | 1.15 | 4.55 | 10.60 | 17.7 |
| GK/C | 3.99 | 1.19 | 4.68 | 10.80 | 20.9 |
| GK/D | 2.84 | 1.18 | 4.70 | 10.96 | 21.5 |

Both SEM and Malvern analysis indicate that the particle size distribution of the fine particles do not substantially change in comparison to the particle size of the starting particles of alpha-lactose monohydrate. Moreover, MgSt shows a good homogeneity inside the blend.

Batches 1C, 1D, 2C and 2D showed an extent of MgSt coating ranging from 60 to 65%, indicating that a higher speed of rotation could contribute to improvement of the extent of coating.

Example 3

Preparation of the Fraction of Fine Particles a) Using the Cyclomix Apparatus

About 25 g of alpha-lactose monohydrate mixed with 2% w/w of magnesium stearate were fed into the stationary conical vessel of a 5 liter laboratory model CYCLOMIX™ apparatus (Hosokawa Micron Ltd) and processed at 125 rpm for 20 minutes (batch C23) or at 500 rpm for 10 minutes (batch C24). The obtained particles were collected and subjected to the chemico-physical technological characterization reported in the Example 2.

Batch C23 showed an extent of MgSt coating of 14.9%, while batch C24 showed an extent of MgSt coating of 19.9%.

Example 4

Preparation of the "Carrier" [Fraction a)+Fraction b)]

Samples of the batch GK/C (Example 1) and C23 (Example 3) were separately mixed with fissured coarse particles of α-lactose monohydrate having a mass diameter comprised between 212-355 micron, and obtained by sieving, in the ratio 90:10 percent by weight. The mixing was carried out in a Turbula mixer operating at a rotation speed of 32 rpm for a period of 240 minutes. The resulting mixtures of particles are termed hereinafter as carriers MF (deriving from mechano-fusion) and CY (deriving from Cyclomix).

Example 5

Preparation of the Dry Powder Formulations

A portion of each carrier as obtained in Example 4 was mixed with micronized formoterol fumarate dihydrate (FF) in a Turbula mixer for 30 minutes at 32 r.p.m. and the resulting blend was forced through a sieve with mesh size of 0.3 mm (300 micron). Micronized beclometasone dipropionate (BDP) and glycopyrronium bromide (GB) and the remaining part of the carrier were blended in a Turbula mixer for 120 minutes at 32 r.p.m. with the sieved mixture to obtain the final formulations MF and CY. Each final formulation was passed through a sieve with mesh size of 0.4 mm (400 micron).

The ratio of the active ingredients to 10 mg of the carrier is 6 microg (μg) of FF dihydrate (theoretical delivered dose 4.5

μg), 100 microg (μg) of BDP and 12.5 microg (μg) of glycopyrronium bromide (theoretical delivered dose 10.0 μg).

The powder formulations MF and CY were characterized in terms of the uniformity of distribution of the active ingredients and aerosol performances after loading it in the multi-dose dry powder inhaler described in WO 2004/012801, which is incorporated herein by reference in its entirety.

The uniformity of distribution of the active ingredients was evaluated by withdrawing 12 samples from different parts of the blend and evaluated by HPLC. The results (mean value±RSD) are reported in Table 3.

The evaluation of the aerosol performance was carried out using the Andersen Cascade Impactor (ACI) according to the conditions reported in the European Pharmacopeia $6^{th}$ Ed 2008, par 2.9.18, pages 293-295, which is incorporated herein by reference in its entirety. After aerosolization of 3 doses from the inhaler device, the ACI apparatus was disassembled and the amounts of drug deposited in the stages were recovered by washing with a solvent mixture and then quantified by High-Performance Liquid Chromatography (HPLC). The following parameters, were calculated: i) the delivered dose which is the amount of drug delivered from the device recovered in the all parts of impactor; ii) the fine particle mass (FPM) which is the amount of delivered dose having a particle size equal to or lower than 5.0 micron and the extrafine FPM which is the amount of delivered dose having a particle size equal to or lower than 2.0 micron; iii) the fine particle fraction (FPF) which is the percentage of the fine particle dose; and iv) the MMAD. The results (mean value±S.D) are reported in Table 3.

TABLE 3

|  | Batch MF | Batch CY |
|---|---|---|
| FF | | |
| Uniformity of distribution | 100.0 (±3.4) | 97.9 (±1.6) |
| Delivered Dose [μg] | 5.3 (±0.1) | 5.2 (±0.4) |
| Fine Particle Mass <5 μm [μg] | 4.3 | 4.0 |
| Fine Particle Fraction <5 μm [%] | 75.0 | 75.9 |
| Extrafine Particle Mass <2 μm [μg] | 3.2 | 3.0 |
| Extrafine Particle Fraction <2 μm [%] | 60.4 | 57.7 |
| MMAD [μm] | 1.2 | 1.2 |
| GB | | |
| Uniformity of distribution | 100.0 (±3.6) | 101.6 (±2.3) |
| Delivered Dose [μg] | 10.8 (±0.5) | 10.5 (±0.6) |
| Fine Particle Mass <5 μm [μg] | 6.4 | 6.6 |
| Fine Particle Fraction <5 μm [%] | 53.8 | 57.2 |
| Extrafine Particle Mass <2 μm [μg] | 4.0 | 4.0 |
| Extrafine Particle Fraction <2 μm [%] | 37.0 | 38.1 |
| MMAD [μm] | 1.8 | 1.8 |
| BDP | | |
| Uniformity of distribution | 99.9 (±3.2) | 99.8 (±1.5) |
| Delivered Dose [μg] | 84.1 (±3.1) | 83.8 (±5.6) |
| Fine Particle Mass [μg] | 66.9 | 64.5 |
| Fine Particle Fraction [%] | 69.9 | 71.2 |
| Extrafine Particle Mass <2 μm [μg] | 50.0 | 48.8 |
| Extrafine Particle Fraction <2 μm [%] | 59.5 | 58.2 |
| MMAD [μm] | 1.1 | 1.1 |

From the data in Table 3, it can be appreciated that the prepared formulations show an excellent homogeneity, an acceptable delivered dose, and a high respirable fraction (FPF), for all the three active ingredients.

They also give rise to a high fraction of particles having a diameter equal or less than 2 microns (at least more than 35% for all the active ingredients), indicating that could be suitable for the prevention and/or treatment of the diseases affecting the distal tract of the respiratory tree.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A dry powder formulation for use in a dry powder inhaler (DPI) to deliver by inhalation a combination of micronized particles of an anticholinergic, an inhaled corticosteroid (ICS), and a long-acting $\beta_2$-agonist (LABA) as active ingredients in a combined therapeutically effective dose of 100 to 500 μg, comprising:
   (a) a fraction of fine particles, comprising a mixture, prepared by co-mixing 90 to 99.5 percent by weight of micronized particles of a physiologically acceptable excipient and 0.5 to 10 percent by weight of magnesium stearate, wherein at least 90% of all said particles have a volume diameter lower than 15 microns and the volume median diameter of said particles is from 3 to 7 microns;
   (b) a fraction of coarse particles comprising a physiologically acceptable excipient having a mass median diameter equal to or higher than 175 microns, wherein the ratio between said fine particles (a) and said coarse particles (b) is from 1:99 to 30:70 percent by weight;
   (c) micronized particles of an anticholinergic, micronized particles of an inhaled corticosteroid (ICS), and micronized particles of a long-acting $\beta_2$-agonist (LABA) as active ingredients, wherein at least 90% of the active ingredient micronized particles have a volume diameter lower than 6.0 μm, wherein, upon actuation of said inhaler, at least 35% of the micronized particles of each of the active ingredients have a diameter equal to or less than 2 μm, and wherein the width of the particle size distribution of said micronized particles of active ingredients, expressed as a span, is from 1.2 to 3.0; and
   wherein the active ingredients, upon administration to the respiratory tract by a dry powder inhaler, are capable of reaching the distal tract of the respiratory tree.

2. The dry powder formulation according to claim 1, wherein at least 90% of all said fine particles have a volume diameter lower than 12 microns, and the volume median diameter of said fine particles is from 4 to 6 microns.

3. The dry powder formulation according to claim 1, wherein said LABA is formoterol fumarate dihydrate, said ICS is beclometasone dipropionate, and said anticholinergic is glycopyrronium bromide.

4. The dry powder formulation according to claim 1, wherein the volume median diameter of the micronized particles of all the active ingredients is from 1.2 to 2.5 microns; and no more than 10% of all said micronized particles have a diameter lower than 0.6 microns.

5. The dry powder formulation according to claim 1, wherein at least 90% of all said micronized particles of said active ingredients (c) have a volume diameter equal to or lower than 5.0 microns, and the volume median diameter of said particles is from 1.3 to 2.2 microns.

6. The dry powder formulation according to claim 1, wherein said magnesium stearate coats the surface of said fine particles (a) in such a way that the extent of the surface coating is at least of 10%.

7. The dry powder formulation according to claim 1, wherein said co-mixing is carried out in a high energy apparatus for a period of less than 20 minutes.

8. The dry powder formulation according to claim 1, wherein the excipient of said fine particles comprises lactose.

9. The dry powder formulation according to claim 1, wherein the excipient of said coarse particles (b) comprises lactose.

10. The dry powder formulation according to claim 1, wherein the excipient of said fine particles (a) comprises lactose, and the excipient of said coarse particles (b) comprises lactose.

11. The dry powder formulation according to claim 7, wherein said high energy apparatus is a mechano-fusion apparatus.

12. The dry powder formulation according to claim 1, wherein said magnesium stearate coats the surface of said fine particles (a) in such a way that the extent of the surface coating is at least of 50%.

13. A dry powder inhaler device, containing a dry powder formulation according to claim 1.

14. A method for the treatment of obstructive airways disease, comprising administering an effective amount of a formulation according to claim 1 to a subject in need thereof.

15. The method according to claim 14, wherein said obstructive airways disease is chronic obstructive pulmonary disease.

16. A process for preparing a dry powder formulation for use in a dry powder inhaler (DPI) to deliver by inhalation a combination of micronized particles of an anticholinergic, an inhaled corticosteroid (ICS), and a long-acting ($\beta_2$-agonist (LABA) as active ingredients in a combined therapeutically effective dose of 100 to 500 μg, comprising:

(a) providing a fraction of fine particles, comprising a mixture, prepared by co-mixing 90 to 99.5 percent by weight of micronized particles of a physiologically acceptable excipient and 0.5 to 10 percent by weight of magnesium stearate, wherein at least 90% of all said particles have a volume diameter lower than 15 microns and the volume median diameter of said particles is from 3 to 7 microns;

(b) providing a fraction of coarse particles comprising a physiologically acceptable excipient having a mass median diameter equal to or higher than 175 microns, wherein the ratio between said fine particles (a) and said coarse particles (b) is from 1:99 to 30:70 percent by weight;

(c) providing micronized particles of an anticholinergic, micronized particles of an inhaled corticosteroid (ICS), and micronized particles of a long-acting $\beta_2$-agonist (LABA) as active ingredients, wherein at least 90% of the active ingredient micronized particles have a volume diameter lower than 6.0 μm, wherein, upon actuation of said inhaler, at least 35% of the micronized particles of each of the active ingredients have a diameter equal to or less than 2 μm, and wherein the width of the particle size distribution of said micronized particles of active ingredients, expressed as a span, is from 1.2 to 3.0; and (d) mixing said fraction of fine particles provided in step (a), said fraction of coarse particles provided in step (b), said micronized particles of an anticholinergic provided in step (c), said micronized particles of an ICS provided in step (c), and said micronized particles of a LABA provided in step (c);

wherein the active ingredients, upon administration to the respiratory tract by a dry powder inhaler, are capable of reaching the distal tract of the respiratory tree.

\* \* \* \* \*